US007670834B2

(12) United States Patent
Fawcett et al.

(10) Patent No.: US 7,670,834 B2

(45) Date of Patent: Mar. 2, 2010

(54) GAS THERMAL CYCLER

(75) Inventors: Adrian Fawcett, Pleasanton, CA (US); Mark T. Reed, Menlo Park, CA (US)

(73) Assignee: Applied Biosystems, LLC, Carlsbad, CA (US)

(*) Notice: Subject to any disclaimer, the term of this patent is extended or adjusted under 35 U.S.C. 154(b) by 1284 days.

(21) Appl. No.: 11/166,958

(22) Filed: Jun. 23, 2005

(65) Prior Publication Data

US 2006/0024816 A1 Feb. 2, 2006

Related U.S. Application Data

(60) Provisional application No. 60/582,524, filed on Jun. 23, 2004.

(51) Int. Cl.
*C12M 1/00* (2006.01)
*C12M 3/00* (2006.01)

(52) U.S. Cl. .................................................. 435/303.1

(58) Field of Classification Search ............... 435/303.1
See application file for complete search history.

(56) References Cited

U.S. PATENT DOCUMENTS

| | | | | |
|---|---|---|---|---|
| 5,187,084 | A | 2/1993 | Hallsby | |
| 5,576,218 | A | 11/1996 | Zurek et al. | |
| 5,783,439 | A | 7/1998 | Richter | |
| 5,795,547 | A | 8/1998 | Moser | |
| 6,337,435 | B1 * | 1/2002 | Chu et al. | 136/242 |
| 6,472,186 | B1 | 10/2002 | Quintanar | |
| 6,482,615 | B2 | 11/2002 | Tal | |
| 6,633,785 | B1 | 10/2003 | Kasahara et al. | |
| 7,081,226 | B1 * | 7/2006 | Wittwer et al. | 422/68.1 |
| 2003/0170883 | A1 * | 9/2003 | Martin et al. | 435/288.4 |
| 2003/0173062 | A1 * | 9/2003 | Lomax et al. | 165/82 |
| 2003/0219754 | A1 * | 11/2003 | Oleksy et al. | 435/6 |
| 2005/0064583 | A1 * | 3/2005 | Caruso et al. | 435/287.2 |
| 2005/0255586 | A1 * | 11/2005 | Shin et al. | 435/303.1 |

FOREIGN PATENT DOCUMENTS

WO WO 98/20975 A1 5/1998

OTHER PUBLICATIONS

Swerdlow, et al., *Rapid Cycle Sequencing in an Air Thermal Cycler*, BioTechniques, 1993, pp. 512-519, vol. 15, No. 3.

International Search Report from International application No. PCT/US2005/022600, mailed Nov. 23, 2005; along with Written Opinion of the International Searching Authority.

* cited by examiner

*Primary Examiner*—Walter D Griffin
*Assistant Examiner*—Lydia Edwards

(57) ABSTRACT

The present application relates to an apparatus and method for thermal cycling using a source of cooling gas.

24 Claims, 12 Drawing Sheets

FIG. 3a
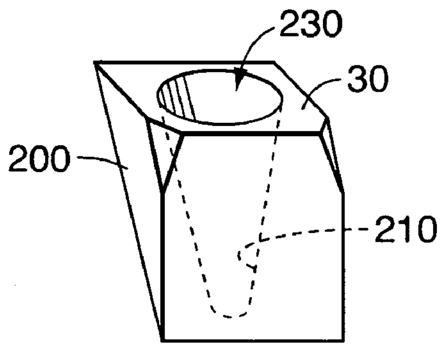
FIG. 3b
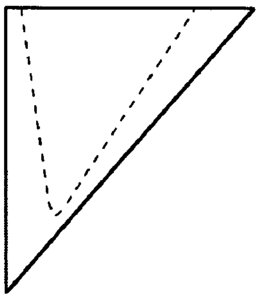
FIG. 3c
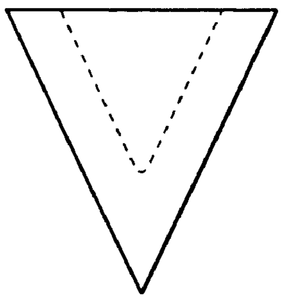
FIG. 3d
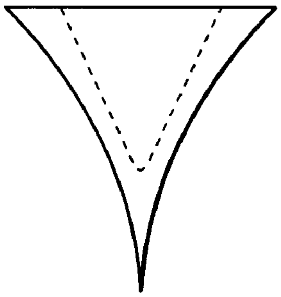
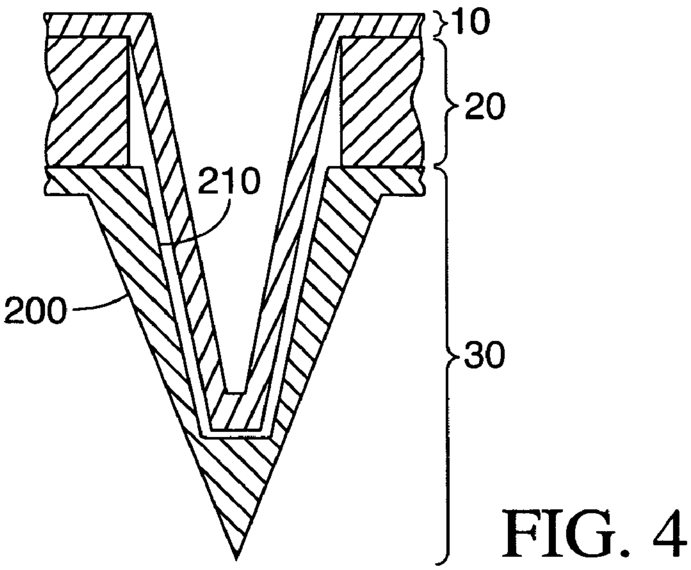
FIG. 4

GAS THERMAL CYCLER

CROSS-REFERENCE TO RELATED APPLICATIONS

This application claims a priority benefit under 35 U.S.C. § 119(e) from U.S. Patent Application No. 60/582,524, filed Jun. 23, 2004, which is incorporated herein by reference.

FIELD

The present application relates to an apparatus and method for thermal cycling using a cooling gas.

INTRODUCTION

Thermal cycling of biological reactions can utilize different types of heat transfer. Heat transfer for thermal cycling can include conduction, radiation, and/or convection to transfer heat from one or more sample wells and to control the temperature during thermal cycling.

Examples of reactions of biological samples include polymerase chain reaction (PCR) and other reactions such as ligase chain reaction, antibody binding reaction, oligonucleotide ligation assays, and hybridization assays. In PCR, biological samples can be thermally cycled through a temperature-time protocol that includes denaturing DNA into single strands, annealing primers to the single strands, and extending those primers to make new copies of double-stranded DNA. Typical thermal cyclers utilize active cooling through the use of thermoelectric coolers such as Peltier devices. During thermal cycling, in certain instances, it is desirable to provide thermal cycling without active cooling. Typical thermal cyclers provide different temperature profiles in a single protocol by utilizing different active coolers or different refrigerants to cool the samples. During thermal cycling, in certain instances, it is desirable to provide thermal cycling with different temperature profiles without using different active coolers or different refrigerants.

SUMMARY

The present teachings can provide a device for thermal cycling of biological samples including a plurality of retaining elements, where each retaining element is adapted to receive a well containing the biological sample, and a source of cooling gas, such that each retaining element includes an inner surface adapted to releasably couple to each well and an outer surface adapted to provide a heat transfer fin for cooling the biological sample in the well with the cooling gas.

The present teachings can provide a method for thermal cycling biological samples including providing a plurality of retaining elements adapted to receive a plurality of wells containing the biological samples, and wherein each retaining element includes an inner surface adapted to releasably couple to each well and an outer surface adapted to cool the biological samples with a source of cooling gas, positioning the plurality of wells such that each well couples to the inner surface of the retaining elements, heating the biological samples, and cooling the biological samples with the cooling gas.

The present teachings can provide a device for thermal cycling of biological samples including means for containing the biological samples, where these means for containing can provide cooling with a cooling gas, and means for heating the biological samples to provide different thermal profiles for the biological samples.

The present teachings can provide a system for thermal cycling of biological samples including a plurality of retaining elements adapted to receive a plurality of wells containing the biological samples, an excitation light source adapted to induce fluorescent light to be emitted by the biological samples during thermal cycling, a source of cooling gas, and a detector adapted to collecting the fluorescent light emitted, where each retaining element includes an inner surface adapted to releasably couple to each well and an outer surface adapted to provide a heat transfer fin for cooling the biological sample in the well with the cooling gas.

It is to be understood that both the foregoing general description and the following description of various embodiments are exemplary and explanatory only and are not restrictive.

BRIEF DESCRIPTION OF THE DRAWINGS

The accompanying drawings, which are incorporated in and constitute a part of this specification, illustrate various embodiments. In the drawings.

FIGS. 3A-3D illustrates cross-sectional views of the inner surface and outer surface of retaining elements according to various embodiments;

FIG. 4 illustrates a cross-sectional side view of the releasable coupling of a sample well with the inner surface of a retaining element according to various embodiments;

DESCRIPTION OF VARIOUS EMBODIMENTS

Figure 1:
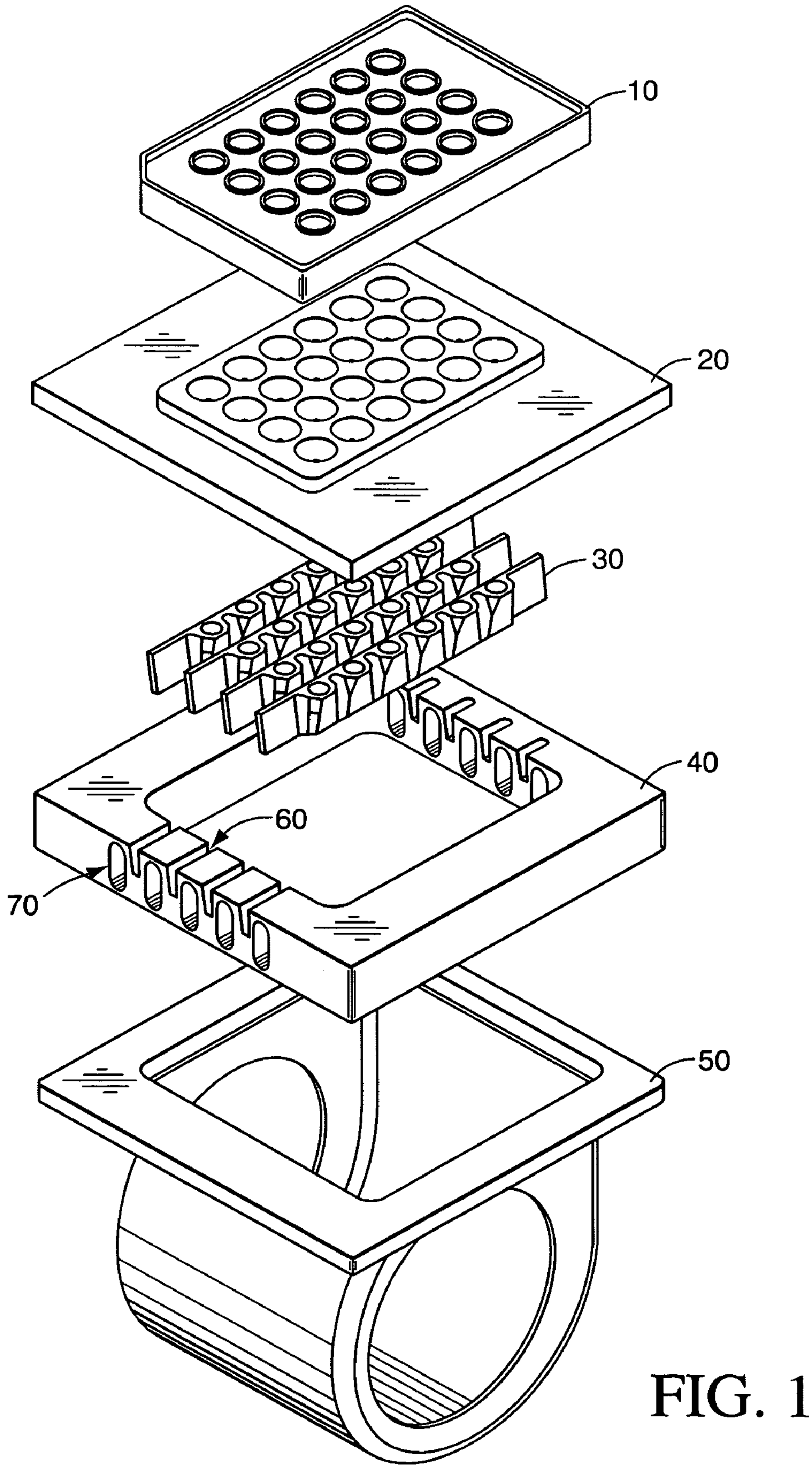
FIG. 1 illustrates a blown-up perspective view of a thermal cycling device according to various embodiments.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting.

Also, terms such as "element" or "component" encompass both elements and components comprising one unit and elements and components that comprise more than one subunit unless specifically stated otherwise. Wherever possible, the same reference numbers will be used throughout the drawings to refer to the same or like parts.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose. In the event that one or more of the incorporated literature and similar materials differs from or contradicts this application, including but not limited to defined terms, term usage, described techniques, or the like, this application controls.

The term "retaining element" or "retaining elements" as used herein refer to the component into which sample wells are positioned to be thermally cycled. The retaining element provides containment for wells and thermal mass for heating and cooling during the thermal cycling. The retaining element can provide a single cavity that holds the sample well or a collection of several cavities in a variety of forms such as a strip of cavities or an array of cavities. The retaining element includes an outer surface oriented in a direction such that it contacts the cooling gas and an inner surface oriented in a direction such that it couples with the sample wells. The retaining elements can have varying physical dimensions and can be adapted to provide different thermal profiles to the biological samples in the sample wells.

The term "heat transfer fin" as used herein refers to the portion of retaining element contacting the cooling gas. The heat transfer fin is adapted to provide sufficient surface area such that the outer surface of retaining element can dissipate sufficient heat during the annealing step of thermal cycling.

The term "wells" as used herein refers to any structure that provides containment to the sample. The wells can be open or transparent to provide entry to excitation light and exit to fluorescent light. The transparency can be provided glass, plastic, fused silica, etc. The well can take any shape including a tube, a vial, a cuvette, a tray, a multi-well tray, a microcard, a microslide, a capillary, an etched channel plate, a molded channel plate, an embossed channel plate, etc. The wells can be part of a combination of multiple wells grouped into a row, an array, an assembly, etc. Multi-well arrays can include 12, 24, 36, 48, 96, 192, 384, or more, sample wells. The wells can be shaped to a multi-well tray under the SBS microtiter format.

The term "heater" as used herein refers to devices that provide heat. Heaters can include, but are not limited to, resistive heaters and convective heaters (i.e., forced-air heaters). An example of a resistive heater that can be pasted to a flat surface of the retaining elements is described in Shin et al., Ser. No. 10/848,593, for "Pasting Edge Heater" filed May 17, 2004 contemporaneously with this application and incorporated herein for such teachings.

The term "blower" as used herein refers to a system to force the cooling gas over the retaining elements. In various embodiments, the blower can be a fan, compressor, compressed gas, nozzle, or other mechanical configuration to increase the pressure of cooling gas known in the art of momentum transfer.

The term "thermal cycling" as used herein refers to heating, cooling, temperature ramping up, and/or temperature ramping down. The thermal cycling determines a thermal profile for a biological sample. In various embodiments, thermal cycling during temperature ramping up can include heating a sample above ambient temperature (20° C.). In various embodiments, thermal cycling during temperature ramping down can include cooling the sample above ambient temperature (20° C.). In various embodiments, post-thermal cycling chilling can include cooling the sample to below ambient temperature (20° C.).

The term "sample" as used herein includes any reagents, solids, liquids, and/or gases. Exemplary samples may comprise anything capable of being thermally cycled.

The term "thermoelectric module" as used herein refers to Peltier devices, also known as thermoelectric coolers (TEC), that are solid-state devices that function as heat pumps. In various embodiments, the thermoelectric module can comprise two ceramic plates with a bismuth telluride composition between the two plates. In various embodiments, when an electric current can be applied, heat is moved from one side of the device to the other, where it can be removed with a heat sink and/or a thermal diffusivity plate. In various embodiments, the "cold" side can be used to pump heat out of a thermal block assembly. In various embodiments, if the current is reversed, the device can be used to pump heat into the thermal block assembly. In various embodiments, thermoelectric modules can be stacked to achieve an increase in the cooling and heating effects of heat pumping. Thermoelectric modules are known in the art and manufactured by several companies, including, but not limited to, Tellurex Corporation (Traverse City, Mich.), Marlow Industries (Dallas, Tex.), Melcor (Trenton, N.J.), and Ferrotec America Corporation (Nashua, N.H.).

The term "excitation light source" as used herein refers to a source of irradiance that can provide excitation that results in fluorescent emission. Light sources can include, but are not limited to, white light, halogen lamp, lasers, solid state laser, laser diode, micro-wire laser, diode solid state lasers (DSSL), vertical-cavity surface-emitting lasers (VCSEL), LEDs, phosphor coated LEDs, organic LEDs (OLED), thin-film electroluminescent devices (TFELD), phosphorescent OLEDs (PHOLED), inorganic-organic LEDs, LEDs using quantum dot technology, LED arrays, filament lamps, arc lamps, gas lamps, and fluorescent tubes. Light sources can have high irradiance, such as lasers, or low irradiance, such as LEDs. The different types of LEDs mentioned above can have a medium to high irradiance.

The term "detector" as used herein refers to any component, portion thereof, or system of components that can detect light including a charged coupled device (CCD), back-side thin-cooled CCD, front-side illuminated CCD, a CCD array, a photodiode, a photodiode array, a photo-multiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and/or manipulation of data, for example, a computer, or other signal processing system.

Figure 2:
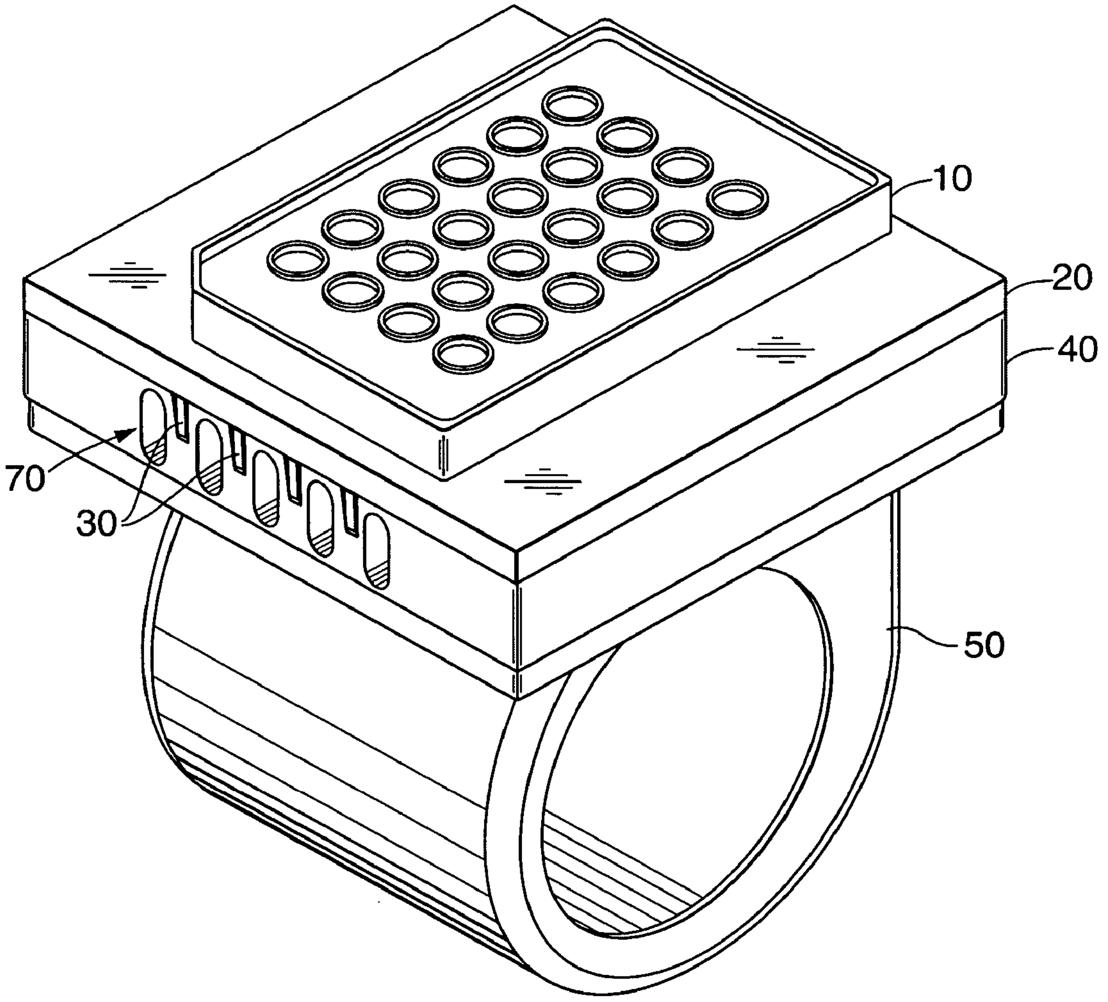
FIG. 2 illustrates an assembled perspective view of the thermal cycling device illustrated in FIG. 1 according to various embodiments.

According to various embodiments, as illustrated in FIGS. 1-2, a thermal cycler device can include upper frame 20, retaining elements 30, lower frame 40, and blower duct 50. According to various embodiments, as illustrated in FIG. 4, tray 10 with sample wells can be positioned to fit through the openings of upper frame 20 and into the retaining elements 30 to releasably couple to the inner surface 210 of retaining element 30. The tray illustrated has 48 wells, but the present teachings can be applied to any sample well. According to various embodiments, the retaining elements 30 can be held in place by slots 60 in lower frame 40. According to various embodiments, as illustrated in FIGS. 5B-5C, heaters 130 can be coupled to the flat surface 120 of the outer surface 200 of retaining elements 30. According to various embodiments, as illustrated in FIGS. 1-2, lower frame 40 can be in contact with blower duct 50 to provide passage to the cooling gas provided by a blower (not shown). The blower duct 50 can channel the cooling gas through lower frame 40 to contact retaining elements 30 and exhaust through vents 70.

According to various embodiments, the heaters can be resistive heaters mounted on the retaining elements. The heaters can be mounted using a variety of coupling means including printing heater elements with conductive inks on the retaining elements. According to various embodiments, the retaining elements that can be heated differently depending on the current provided to the heaters mounted to each retaining elements to provide different temperature profiles. According to various embodiments, the retaining elements can be constructed of conductive polymers and thereby provide the resistive heating when current is passed through the retaining element. According to various embodiments, the slots and/or vents in lower frame can provide access for the electrical connections for the heaters.

According to various embodiments, the heaters can be convective heaters providing a heating gas. Such as stream can be provided through the blower duct. The heating gas can be heated by a resistive heater. According to various embodiments, the cooling gas can be cooled by a thermoelectric module located in the path of the gas. Cooling the gas with a thermoelectric module is unlike cooling samples because the thermoelectric module is unidirectional (cooling only) and does not conform to the time constraints of the thermal cycling.

According to various embodiments, as illustrated in FIGS. 5B-5C, the retaining elements 30 can include a flat surface 120 portion of the outer surface 200 for coupling with the heater 130 to contain the lower portion of the sample well. The thickness of retaining element 30 between the flat surface 120 and inner surface 210 can be adapted to provide substantial thermal uniformity to the samples according to the heater properties and thermal conductance of the retaining element 30. The inner surface 210 of the retaining element 30 can be adapted to provide heat to the sample well surface sufficient to thermally cycle the sample in the sample well.

According to various embodiments, the retaining elements reduce the thermal mass of the component in contact with the sample wells. Reduction of the thermal mass permits rapid cooling of the biological samples. According to various embodiments, retaining elements 30 can provide a flat surface 120, as illustrated in FIGS. 5B-5C, or they can not provide a flat surface, as illustrated in FIGS. 7-8.

According to various embodiments, as illustrated in FIGS. 3A-3D, retaining elements can have a variety of thicknesses. The thickness between inner surface 210 and outer surface 200 of the retaining elements 30 can vary, while providing a cavity 230 of similar volume for the sample well. According to various embodiments, the thickness between the inner surface 210 and outer surface 200 can be uniform or can differ at different points on the inner surface 210 and outer surface 200. For example, FIG. 3C illustrates a retaining element 30 where the inner surface 210 has the same shape as the outer surface 200. Such a configuration as FIG. 3C has a uniform thickness. Whereas, FIG. 3D illustrates a retaining element 30 where the inner surface 210 has a different shape than the outer surface 200. Such a configuration as FIG. 3D provides a different thickness between the inner surface 210 and the outer surface 200, as can be seen by the difference in thickness at the top part of the cavity 230 (closer to the open mouth) and the bottom part of the cavity 230 (closer to the closed tip).

According to various embodiments, differences in thickness can provide different thermal properties to the retaining elements by providing increased surface area for heat dissipation and/or closer proximity of the sample to the cooling gas.

According to various embodiments, as illustrated in FIGS. 3A-3D, retaining elements 30 can have different outer surfaces 200. According to various embodiments, the outer surfaces 200 can be flat, concave, or convex. According to various embodiments, the outer surfaces 200 can be cylindrical, conical, pyramidal, and/or trapezoidal. According to various embodiments, the outer surfaces 200 can include a flat surface to provide areas to couple resistive heaters. According to various embodiments, the outer surface 200 provides a high surface area per well to permit effective cooling by the cooling gas.

According to various embodiments, the retaining elements in a thermal cycling device can be separately controlled such that different portions of the thermal cycling device provide different temperature profiles to the samples in those portions. This enables the thermal cycling device to perform several thermal profiles within a single protocol for a group of samples. For example, several samples can be run against several tests that include different annealing temperatures. By setting a different annealing temperature for each retaining element, the samples can be arranged according to retaining element to obtain the desired results. In another example, optimal annealing temperature for a given test is unknown. Several conditions can be run in parallel to empirically determine the optimal annealing temperature. As discussed below, thermal cycling methods can be designed to provide such determinations.

Figure 5A:
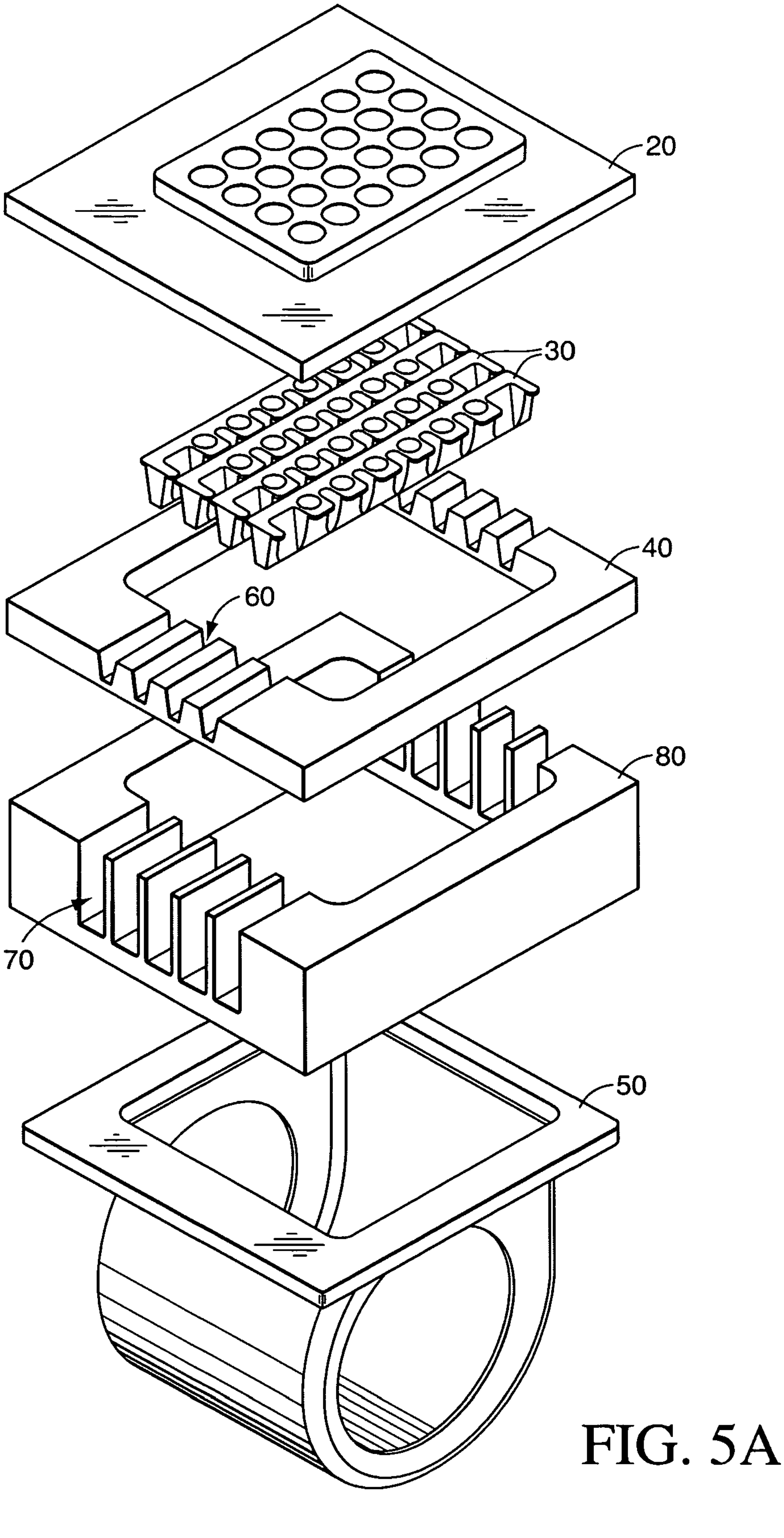
FIG. 5A illustrates a blown-up perspective view of the a thermal cycling device according to various embodiments.
Figure 5B:
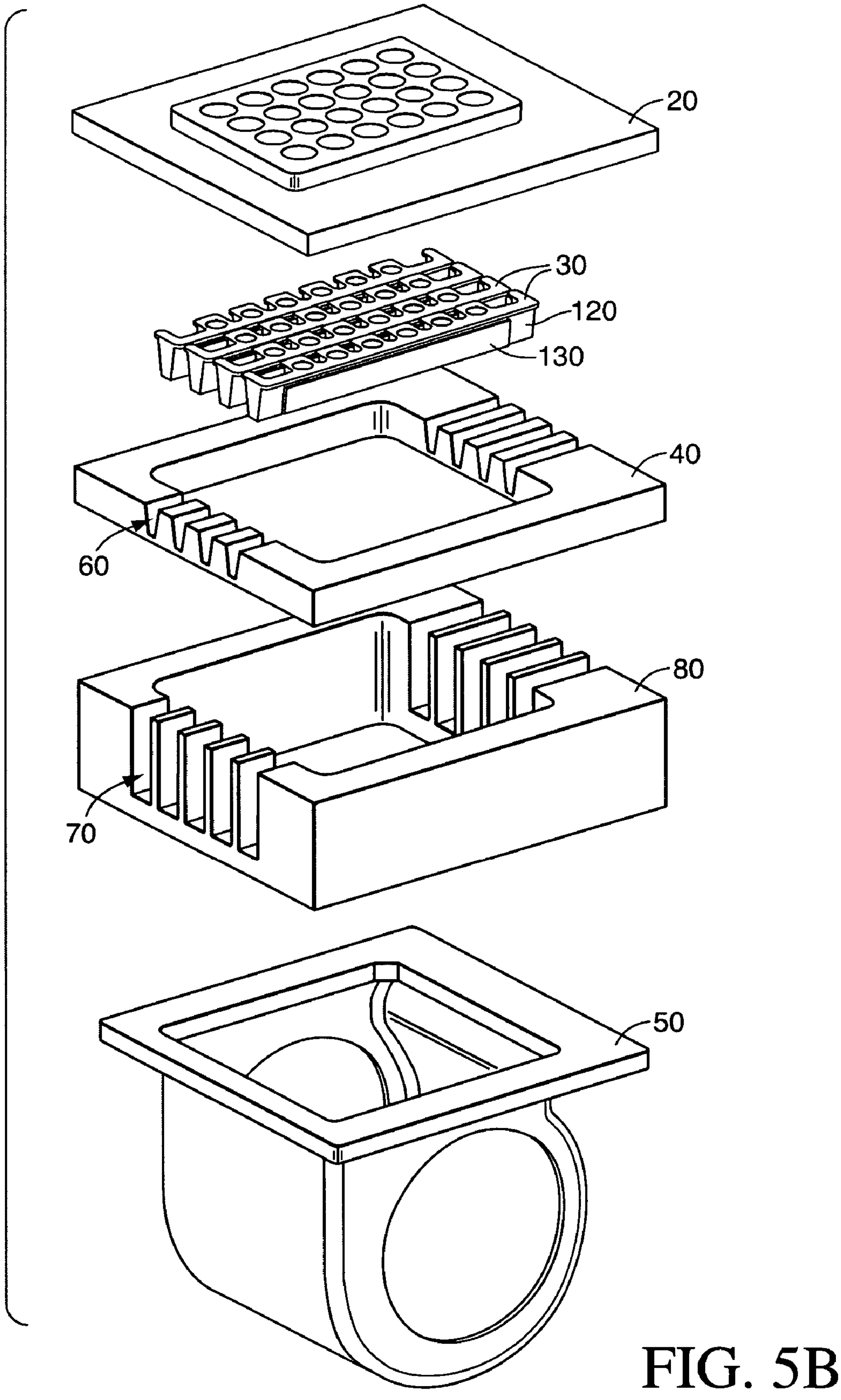
FIG. 5B illustrates a blown-up perspective view of the thermal cycling device in FIG. 5A from the opposite direction.
Figure 5C:
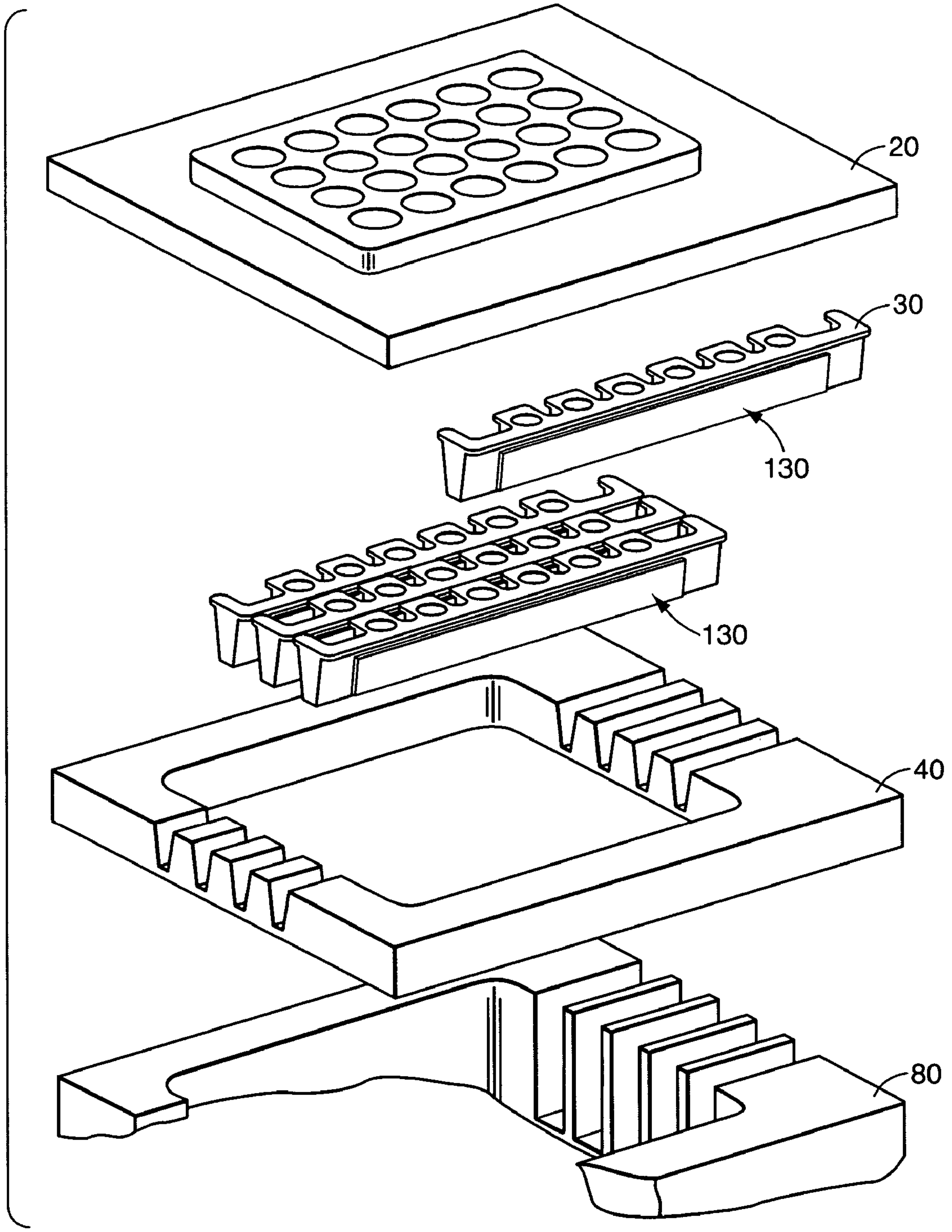
FIG. 5C illustrates a blown-up perspective view of the thermal cycling device in FIG. 5B shifting a strip of retaining elements to show internal details.

According to various embodiments, as illustrated in FIGS. 5A-5C, the thermal cycling device can provide retaining elements 30 with separate control of each retaining element strip by coupling a separate heater 130 to each retaining element strip such that power can be regulated to each heater 130 separately. Such regulation of the heating and cooling of each retaining element strip provides different temperature profiles for the biological samples in the sample wells in each retaining element strip.

According to various embodiments, different retaining elements can be constructed as discussed herein. According to various embodiments, different retaining elements can be constructed by altering the material composition of the retaining element. According to various embodiments, the retaining elements can be constructed of aluminum, silver, gold, copper, and composite materials such as conductive polymers.

According to various embodiments, as illustrate in FIGS. 1-2, the upper frame can lock the retaining elements into the slots of the lower frame at the edges of the frame. According to various embodiments, as illustrated in FIG. 4, the upper frame 20 can surround the upper portion of sample well 10 (above the lower portion that contains the sample and is surrounded by retaining element 30) to minimize optical cross-talk between adjacent sample wells that can cause images of fluorescent light emitted from each sample to overlap on a detector positioned over the sample wells. According to various embodiments, the upper frame 20 can isolate the sample wells from airflow in the surrounding environment (including the cooling gas) that can cause condensation in the sample wells. According to various embodiments, as illustrated in FIGS. 1-2, the upper frame 20 can isolate the sample wells from airflow in the surrounding environment to provide more efficient cooling by the cooling gas and channel the gas from the blower duct 50 to the vents 70 in lower frame 40.

According to various embodiments, as illustrated in FIGS. 1-2, the upper frame 20 can protect a user from exposure to the retaining elements that can be hot surfaces that can reach temperatures in excess of 100 degrees centigrade.

Figure 6A:
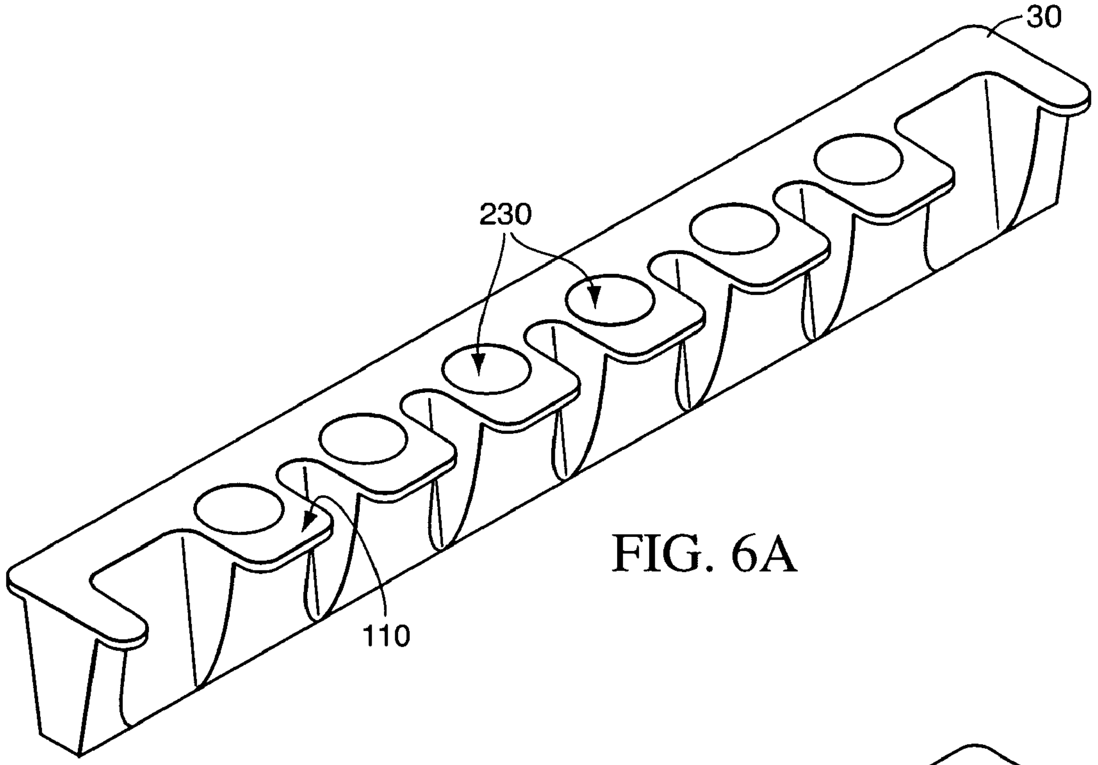
FIGS. 6A-6B illustrate perspective views of strips of retaining elements with a flat surface and with parallel finlets according to various embodiments.
Figure 6B:
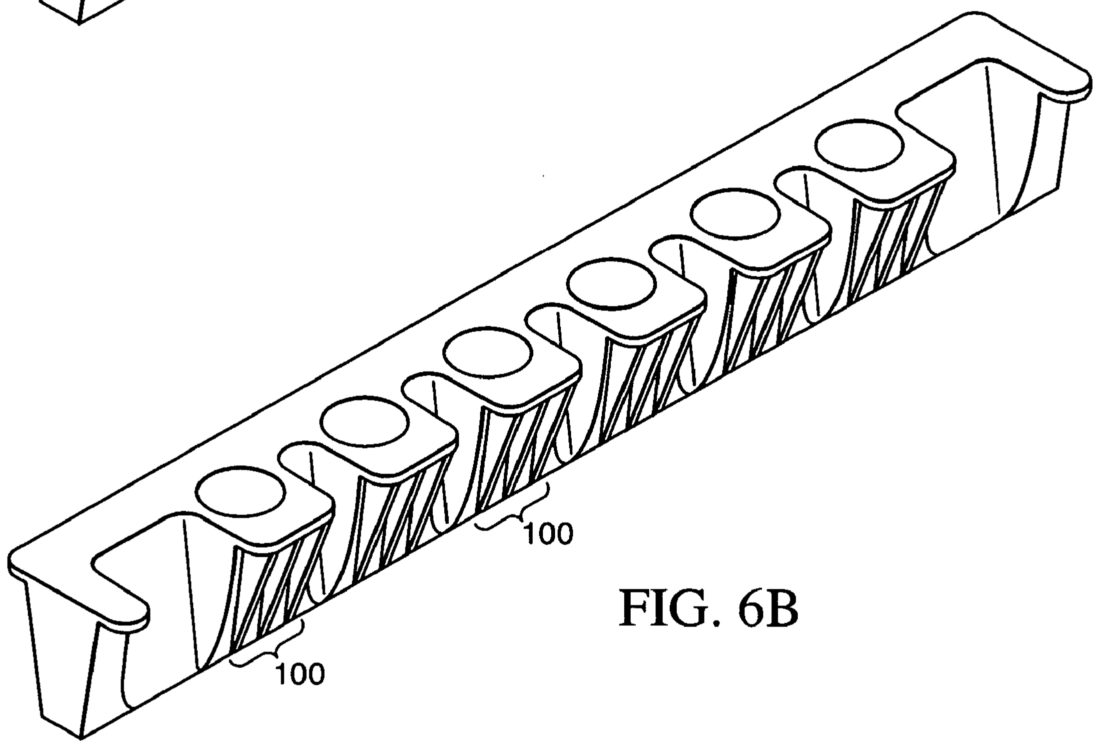
Figure 7A:
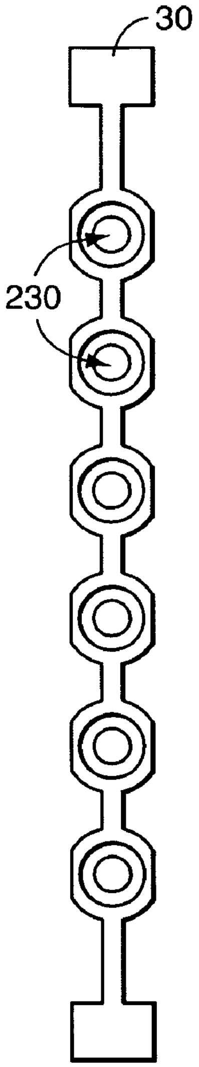
FIG. 7A illustrates a top view and FIG. 7B illustrates a perspective view of strips of retaining elements without a flat surface according to various embodiments.
Figure 7B:
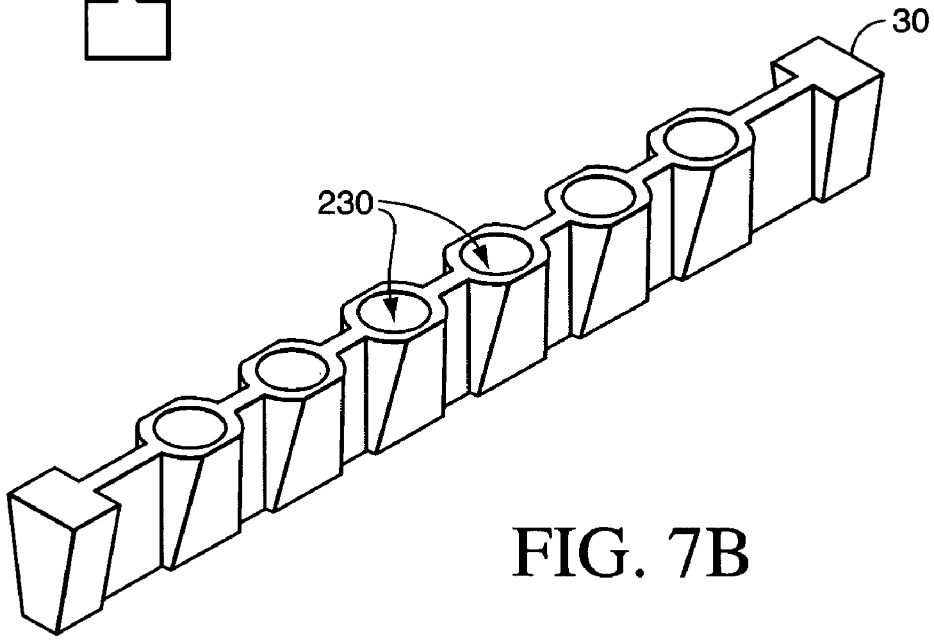
Figure 8A:
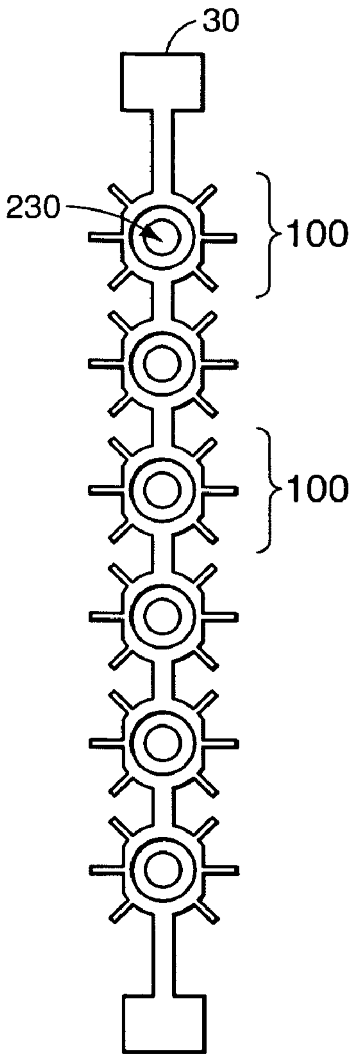
FIG. 8A illustrates a top view and FIG. 8B illustrates a perspective view of strips of retaining elements without a flat surface and with radial finlets according to various embodiments.
Figure 8B:
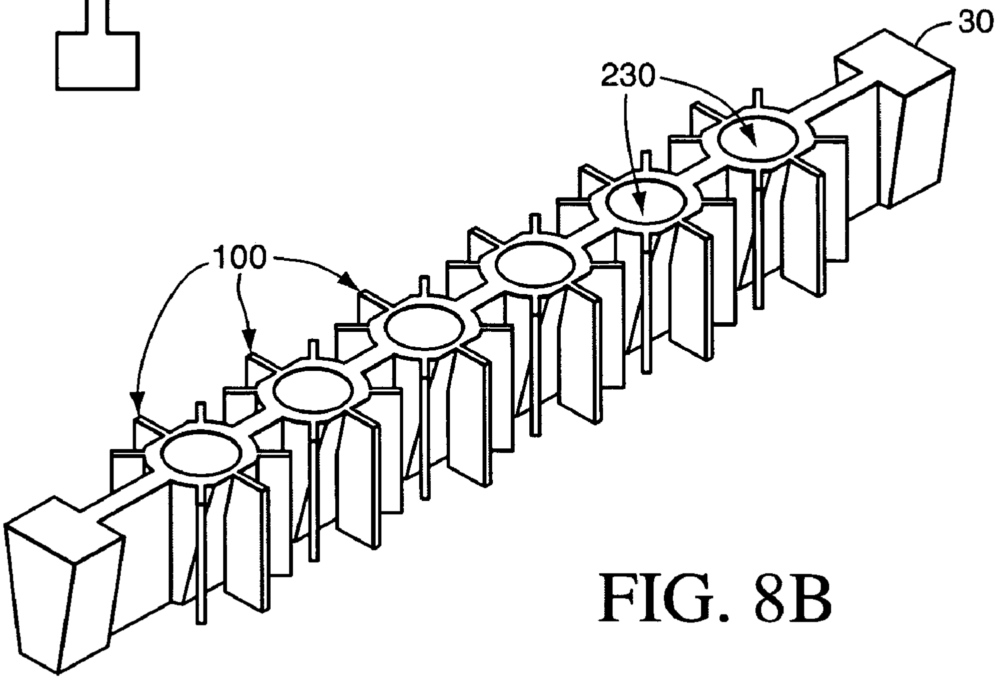

According to various embodiments, as illustrated in FIG. 6A, retaining elements can include a lip 110 to direct the cooling gas away from the tray (not shown). Directing the cooling gas away from the tray provides reduction in the effects of condensation that can interfere with detection of thermal cycling results by a detector (not shown) located above the thermal cycling device. According to various embodiments, as illustrated in FIG. 6B, retaining elements 30 can include finlets 100 that can increase the surface area for heat dissipation of the heat transfer fin to the cooling gas. The finlets can be parallel creating unidirectional channels for the cooling gas. According to various embodiments, the finlets 100 can direct the cooling gas way from the tray to reduce the effects of condensation. According to various embodiments, as illustrated in FIGS. 7A-7B, retaining elements 30 can be tapering without a flat surface and without finlets. According to various embodiments, as illustrated in FIGS. 8A-8B, retaining elements 30 can include finlets 100 that are radial creating multi-directional channels for the cooling gas. According to various embodiments, the finlets can generate turbulence to the cooling gas traveling through the channels created by the finlets to provide increased heat transfer.

Figure 10A:
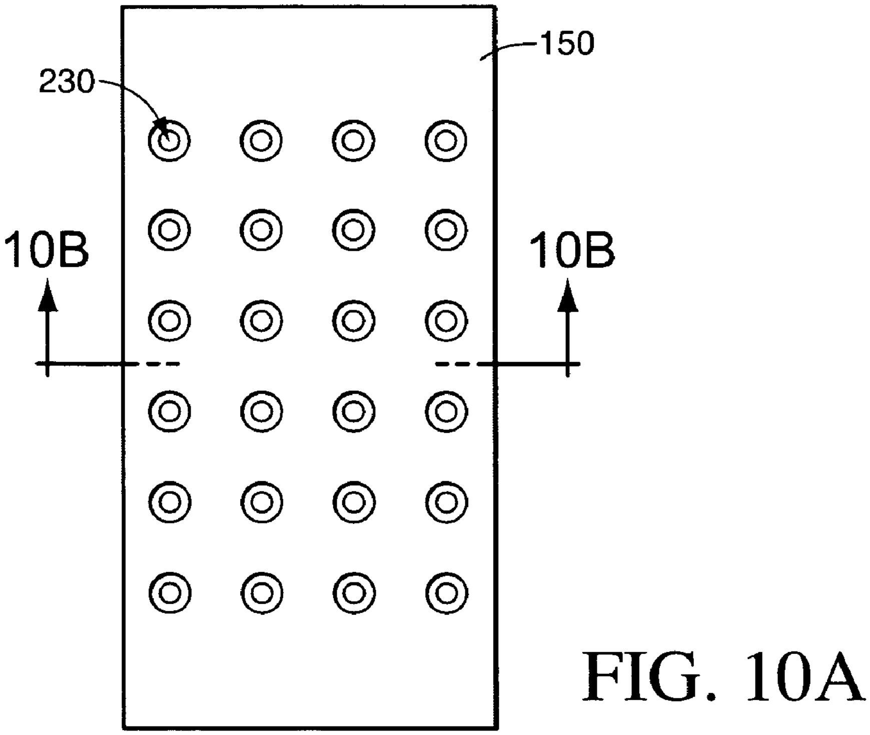
FIG. 10A illustrates a top view, FIG. 10B illustrated a side view along A-plane.
Figure 10B:
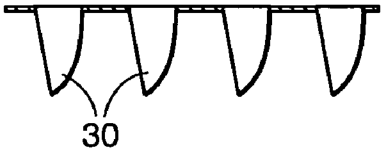
FIG. 10C illustrates a perspective view of a retaining element array according to various embodiments.
Figure 10C:
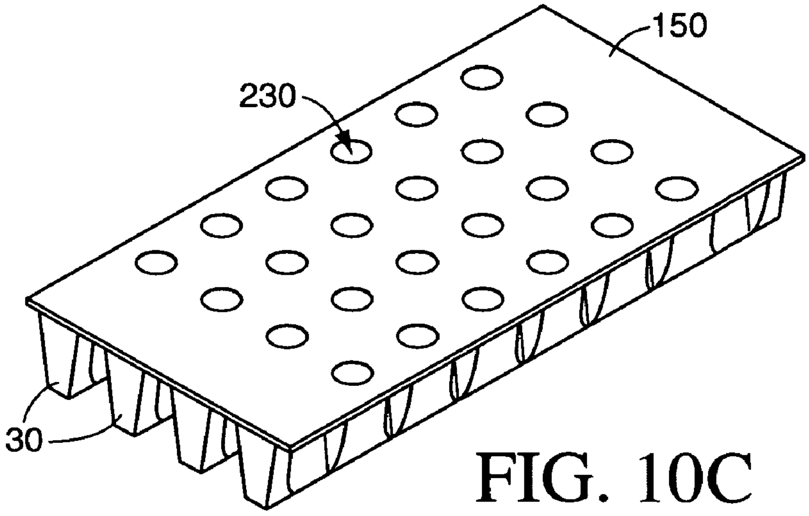

According to various embodiments, as illustrated in FIGS. 10A-10C, retaining elements 30 can form a retaining element array with a unitary top surface 150 with the openings of cavities 230. As shown in FIGS. 10B-10C, the retaining elements 30 below top surface 150 can form strips of retaining elements to channel the cooling gas. According to various embodiments, the retaining element array can include individual retaining elements connected by the unitary top surface. According to various embodiments, the retaining element array can provide uniform heating and cooling to each sample well with one or more heaters jointly controlled.

According to various embodiments, the thermal cycling device can include a detection system including an excitation light source and detector. According to various embodiments, the detection system can be part of a real-time detection scheme throughout the thermal cycling. In real-time thermal cycling, samples can be detected during the thermal cycling, rather than chilling samples after the thermal cycling is complete and then detecting the end-point results of the thermal cycling.

Figure 9A:
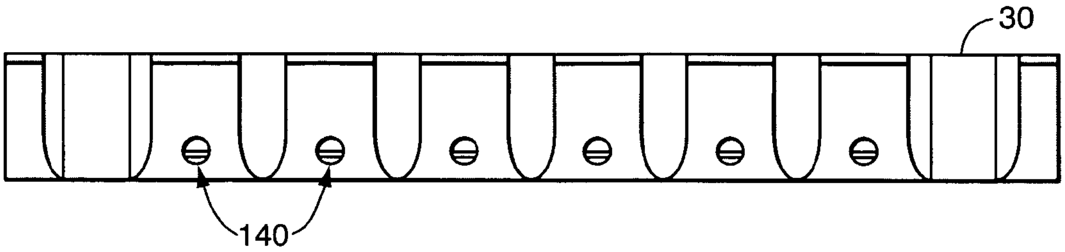
FIG. 9A illustrates a side view and FIG. 9B illustrates a perspective view of strips of retaining elements with a flat surface and an opening between the inner surface and outer surface according to various embodiments.
Figure 9B:
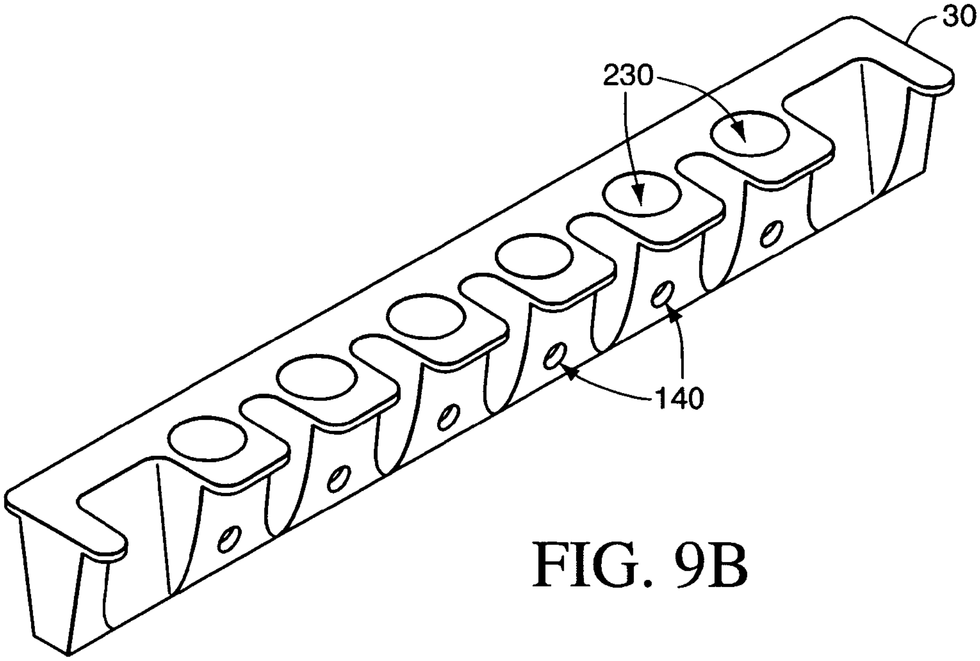

According to various embodiments, as illustrated in FIGS. 9A-9B, each retaining element 30 can include openings 140 between the inner surface and outer surface, wherein the opening is adapted to direct the fluorescent light to the detector. According to various embodiments, an excitation light source can be adapted to induce fluorescent light to be emitted by the biological samples during thermal cycling. According to various embodiments, the excitation light source can be positioned above the sample wells and the detector can be positioned to collect fluorescent light through the opening between the inner surface and outer surface of the retaining element. According to various embodiments, the excitation light source can be positioned proximate to the opening between the inner surface and outer surface of the retaining element and the detector can be positioned above the samples wells. According to various embodiments, the excitation light source can represent a single source (e.g. halogen lamp) or multiple sources (e.g. LEDs). According to various embodiments, the excitation light can have a path that is substantially perpendicular to the fluorescent light path. By having a different light path for the excitation light and the fluorescent light, optical components such as beam-splitters and filters can be eliminated from a thermal cycling system. According to various embodiments, as illustrated in FIGS. 5A-5C, the detector or excitation light source can be positioned in vent frame 80. By positioning the detector or excitation light source in the path of the cooling gas, the detector or excitation light source can be cooled by the cooling gas. Certain detectors (e.g. CCDs) and excitation light sources (LEDs) can require cooling for consistent operation.

According to various embodiments, the sample volumes can be up to 100 microliters. Typical thermal cycling samples are limited to 30 microliters due to thermal restraints of the thermal cycling device. The increased surface area for heating and cooling of the present teachings provides capacity for larger volumes of sample.

According to various embodiments, the thermal cycling device can include a heated lid. The retaining elements can be sufficiently rigid to withstand the force of the heated lid that provides pressure onto the sample wells. According to various embodiments, the upper frame can be releasably connected to the lower frame to provide an ejection system for the sample wells to dislodge them from the retaining elements.

According to various embodiments, the stream of cooling gas is air. According to various embodiments, the stream of cooling gas can be nitrogen or other refrigerant gas.

According to various embodiments, as illustrated in FIGS. 5A-5C, a thermal cycler device can include upper frame 20, retaining elements 30, lower frame 40, vent frame 80, and blower duct 50. According to various embodiments, the retaining elements 30 can be held in place by slots 60 in lower frame 40. According to various embodiments, heaters 130 can be coupled to retaining elements 30 with wiring running through lower frame 40 or vent frame 80. According to various embodiments, lower frame 40 can be in contact with vent frame 80 that can be in contact with blower duct 50 to provide passage to the cooling gas provided by the blower (not shown). The blower duct 50 can channel the cooling gas through vent frame 80 and lower frame 40 to contact retaining elements 30. According to various embodiments, the cooling gas can be deflected by retaining elements 30 to vents 70 in vent frame 80. This can direct the cooling gas away from the tray (not shown). Directing the cooling gas away from the tray provides reduction in the effects of condensation that can interfere with detection of thermal cycling results by a detector (not shown) located above the thermal cycling device.

According to various embodiments, the method of thermally cycling biological samples by heating and cooling with devices according to the present teachings can include annealing the biological samples at different temperatures. According to various embodiments, annealing temperature can be optimized for particular assays to be run on a device for thermal cycling. Optimization permits designing assays that do not conform to the universal conditions for PCR thermal cycling. An example of such is thermal cycling of splice variants where the annealing temperature is increased from the universal conditions.

Figure 11A:
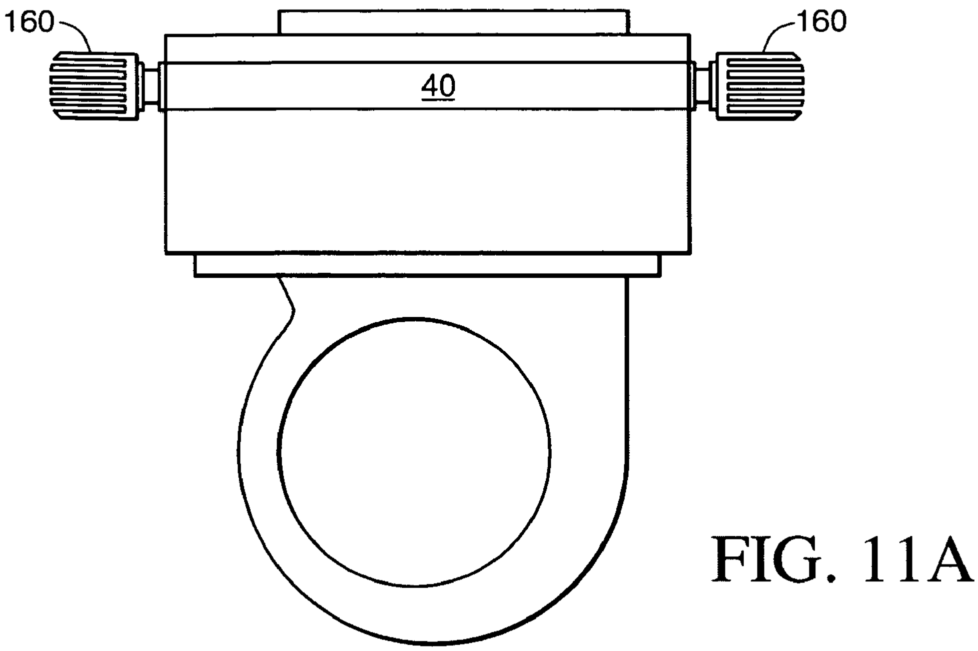
FIG. 11A illustrates a side view and FIG. 11B illustrates a perspective view of the assembled device of FIG. 5A with coolers according to various embodiments.
Figure 11B:
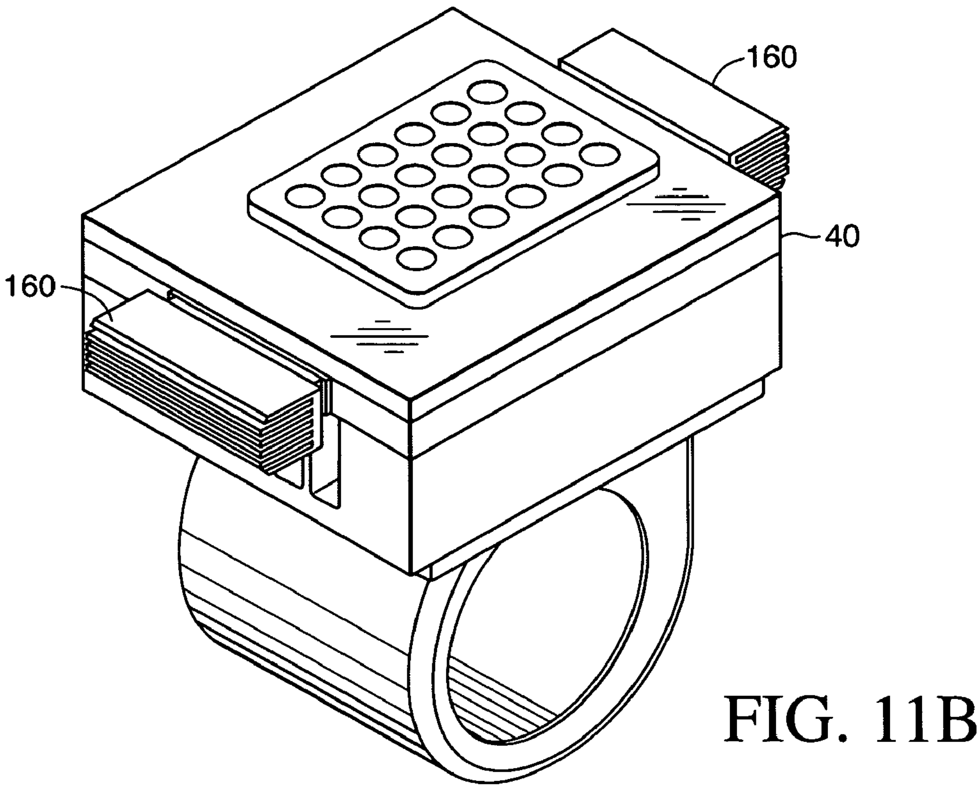

According to various embodiments, as illustrated in FIGS. 11A-11B, the thermal cycling system can include thermoelectric modules 160. The thermoelectric modules can be coupled to frame 40, which can be thermally conductive providing heat pumping from the retaining elements 30 to the environment. Such thermal pumping can provide cooling below ambient temperature (20° C.) and maintaining the biological samples at a temperature below ambient. Cooling below ambient temperature can preserve biological samples after thermal cycling for further analysis or use. According to various embodiments, thermoelectric modules can be coupled to the blower duct or other component in the path of the cooling gas to reduce the temperature of the cooling gas below ambient temperature. According to various embodiments, a method for cooling the biological samples after thermal cycling can include closing vents 70 to permit the cooling gas to recirculate within the frame 40 and vent frame 80 maintaining the biological samples at a temperature below ambient.

What is claimed is:

1. A device for thermal cycling of biological samples, the device comprising:

a plurality of retaining elements, wherein each retaining element is adapted to receive a well containing the biological sample; and a source of cooling gas, wherein each retaining element comprises an inner surface adapted to releasably couple to each well and an outer surface adapted to provide a heat transfer fin for cooling the biological sample in the well with the cooling gas.

2. The device of claim 1, wherein the plurality of retaining elements form a plurality of retaining element strips.

3. The device of claim 2, wherein each strip is adapted to provide a different thermal profile for the biological samples in the wells releasably coupled to the strip.

4. The device of claim 3, wherein the strips are constructed of different material.

5. The device of claim 3, wherein each strip comprises a flat surface.

6. The device of claim 5, wherein each strip comprises a heater coupled to the flat surface, wherein each heater is adapted to separate control.

7. The device of claim 6, wherein the heater is coupled to the flat surface with an adhesive.

8. The device of claim 6, wherein the heater is coupled to the flat surface by printing.

9. The device of claim 3, wherein the plurality of retaining elements are constructed of a thermally conductive and electrically resistive material.

10. The device of claim 9, wherein the material is a conductive polymer.

11. The device of claim 9, wherein each strip is adapted to separate control.

12. The device of claim 3, wherein each strip is adapted to separate control to provide different annealing temperatures to at least one of the strips.

13. The device of claim 1, further comprising a cooler.

14. The device of claim 13, wherein the cooler is adapted to reduce the temperature of the cooling gas below ambient temperature.

15. The device of claim 13, wherein the cooler is coupled to the retaining elements to reduce the temperature of the samples below ambient temperature.

16. The device of claim 1, wherein the plurality of retaining elements form a unitary retaining element array.

17. The device of claim 1, wherein the outer surface comprises finlets.

18. The device of claim 17, wherein the finlets are parallel.

19. The device of claim 17, wherein the finlets are radial.

20. A system for thermal cycling of biological samples, the system comprising:

a plurality of retaining elements adapted to receive a plurality of wells containing the biological samples;

an excitation light source adapted to induce fluorescent light to be emitted by the biological samples during thermal cycling;

a source of cooling gas; and a detector adapted to collecting the fluorescent light emitted, wherein each retaining element comprises an inner surface adapted to releasably couple to each well and an outer surface adapted to provide a heat transfer fin for cooling the biological sample in the well with the cooling gas.

21. The system of claim 20, wherein the system is adapted to reduce the effect of condensation on the biological samples.

22. The system of claim 21, further comprising vents adapted to direct the cooling gas away from the biological samples.

23. The system of claim 20, wherein each retaining element comprises an opening between the inner surface and outer surface, wherein the opening is adapted to direct the fluorescent light to the detector.

24. The system of claim 23, wherein the excitation light has a path that is substantially perpendicular to the fluorescent light path.

* * * * *